United States Patent
Rieping et al.

(12) 
(10) Patent No.: US 6,630,332 B2
(45) Date of Patent: Oct. 7, 2003

(54) PROCESS FOR THE FERMENTATIVE PREPARATION OF L-THREONINE

(75) Inventors: Mechthild Rieping, Blelefeld (DE); Georg Thierbach, Bielefeld (DE); Michel Eduard Van Der Rest, Venlo (NL); Douwe Molenaar, Baesweler (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/801,042

(22) Filed: Mar. 8, 2001

(65) Prior Publication Data

US 2002/0127678 A1 Sep. 12, 2002

Related U.S. Application Data

(60) Provisional application No. 60/229,329, filed on Sep. 1, 2000.

(30) Foreign Application Priority Data

Jul. 18, 2000 (DE) .......................... 100 34 833
Jan. 30, 2001 (DE) .......................... 101 03 874

(51) Int. Cl.$^7$ ................................ C12N 9/02
(52) U.S. Cl. ...................... 435/189; 435/69.1; 435/183; 435/252.3; 435/252.32; 435/320.1; 530/350; 536/23.2
(58) Field of Search ................ 435/69.1, 183, 435/189, 252.3, 252.32, 320.1; 530/350; 536/23.2

(56) References Cited

FOREIGN PATENT DOCUMENTS

| DE | 198 31 609 | 4/1999 |
| EP | 0 436 886 | 7/1991 |
| EP | 1 038 969 | 9/2000 |
| EP | 1 085 091 | 3/2001 |

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief Bioinform. Mar. 2001, vol. 2(1), pp. 19–29.*
Itoh et al. GenBank Accession D90850 AB001340. Mar. 21, 1997 (Alignment No. 1).*
Itoh et al. GenBank Accession D90850 AB001340. Mar. 21, 1997 (Alignment No. 2).*
Kather et al., "Another unusual type of citric acid cycle enzyme in *Helicobacter pylori*: the malate: quinone oxidoreductase", Journal of Bacteriology, vol. 182, No. 11, 2000, pp. 3204–3209.
Molenaar et al., "Biochemical and genetic characterization of the membrane–associated malate dehydrogenase (acceptor) from *Corynebacterium glutamicum*", European Journal of Biochemistry vol. 254, 1998, p. 395–403.
Vogel et al., "Cloning and sequence of the mdh structural gene of *Escherica coli* coding for malate dehydrogenase", Archives of Microbiology, 1987, vol. 149, p. 36–42.
Van Der Rest et al., "Functions of the membrane–associated and cytoplasmic malate dehydrogenase in the citric acid cycle of *Escheria coli*", Journal of Bacteriology, vol. 182, 2000, p. 6892–6899.
English language abstract of FR above.
English language abstract of GR above.
Englishe language abstract of HR above.
English language abstract of IR above.
Database EMBL, accession No. XP002179954.

* cited by examiner

*Primary Examiner*—Ponnathapu Achutamurthy
*Assistant Examiner*—Christian L. Fronda
(74) *Attorney, Agent, or Firm*—Pillsbury Winthrop LLP (57) ABSTRACT

The invention provides a process for the fermentative preparation of L-threonine using Enterobacteriaceae which in particular already produce L-threonine and in which the nucleotide sequence(s) which code(s) for the mqo gene are enhanced, in particular over-expressed.

13 Claims, 1 Drawing Sheet

Figure 1:

SEQUENCE LISTING

```
<160> NUMBER OF SEQ ID NOS: 12

<210> SEQ ID NO 1
<211> LENGTH: 1720
<212> TYPE: DNA
<213> ORGANISM: Escherichia coli
<220> FEATURE:
<221> NAME/KEY: CDS
<222> LOCATION: (7)..(1593)
<223> OTHER INFORMATION: mqo gene

<400> SEQUENCE: 1 aattcg atg gcg gca aaa gcg aaa gcg tcc gag gag cag gaa act gat        48
       Met Ala Ala Lys Ala Lys Ala Ser Glu Glu Gln Glu Thr Asp
         1               5                  10 gta ctg ttg att ggc ggc ggc att atg agc gcc acg ttg ggg acc tat        96
Val Leu Leu Ile Gly Gly Gly Ile Met Ser Ala Thr Leu Gly Thr Tyr
 15                  20                  25                  30 tta cgc gag ctg gag cct gaa tgg tcg atg acc atg gtg gag cgc ctg       144
Leu Arg Glu Leu Glu Pro Glu Trp Ser Met Thr Met Val Glu Arg Leu
                     35                  40                  45 gag ggt gtc gcg cag gag agt tcg aac ggc tgg aat aac gcc gga acc       192
Glu Gly Val Ala Gln Glu Ser Ser Asn Gly Trp Asn Asn Ala Gly Thr
                 50                  55                  60 ggg cat tct gca ctg atg gaa ctg aac tac acc ccg caa aac gcc gat       240
Gly His Ser Ala Leu Met Glu Leu Asn Tyr Thr Pro Gln Asn Ala Asp
             65                  70                  75 ggc agc atc agt att gaa aaa gca gtc gcc att aac gaa gca ttt cag       288
Gly Ser Ile Ser Ile Glu Lys Ala Val Ala Ile Asn Glu Ala Phe Gln
         80                  85                  90 att tcc cgc cag ttc tgg gcg cac cag gtt gag cgc ggc gtg ctg cgt       336
Ile Ser Arg Gln Phe Trp Ala His Gln Val Glu Arg Gly Val Leu Arg
 95                 100                 105                 110 act ccg cgt tca ttt atc aat acc gtt ccg cat atg agc ttt gtc tgg       384
Thr Pro Arg Ser Phe Ile Asn Thr Val Pro His Met Ser Phe Val Trp
                    115                 120                 125
```

-continued

```
ggc gag gat aac gtc aat ttc ctg cgc gcc cgt tac gcc gcg ttg caa       432
Gly Glu Asp Asn Val Asn Phe Leu Arg Ala Arg Tyr Ala Ala Leu Gln
            130                 135                 140 caa agc tcg ctg ttt cgc ggt atg cgt tac tct gaa gat cac gcg cag       480
Gln Ser Ser Leu Phe Arg Gly Met Arg Tyr Ser Glu Asp His Ala Gln
            145                 150                 155 atc aaa gag tgg gca ccg tta gtg atg gaa ggg cgc gat ccg caa cag       528
Ile Lys Glu Trp Ala Pro Leu Val Met Glu Gly Arg Asp Pro Gln Gln
160                 165                 170 aaa gtg gca gcc acg cgt acg gaa att ggt acc gat gtg aac tac ggc       576
Lys Val Ala Ala Thr Arg Thr Glu Ile Gly Thr Asp Val Asn Tyr Gly
175                 180                 185                 190 gag atc acc cgc cag tta att gct tcc ttg cag aag aaa tct aac ttc       624
Glu Ile Thr Arg Gln Leu Ile Ala Ser Leu Gln Lys Lys Ser Asn Phe
                195                 200                 205 tcg ctg caa ctc agc agc gaa gtc cgc gcc cta aag cgt aat gac gat       672
Ser Leu Gln Leu Ser Ser Glu Val Arg Ala Leu Lys Arg Asn Asp Asp
            210                 215                 220 aac acc tgg acc gtt acc gtt gcc gat ctg aaa aat ggc act gca cag       720
Asn Thr Trp Thr Val Thr Val Ala Asp Leu Lys Asn Gly Thr Ala Gln
            225                 230                 235 aac att cgt gcc aaa ttt gtc ttt atc ggc gcg ggt ggt gcg gcg ctg       768
Asn Ile Arg Ala Lys Phe Val Phe Ile Gly Ala Gly Gly Ala Ala Leu
240                 245                 250 aag ctg tta cag gaa tcg ggg att ccg gaa gcg aaa gac tac gcc ggt       816
Lys Leu Leu Gln Glu Ser Gly Ile Pro Glu Ala Lys Asp Tyr Ala Gly
255                 260                 265                 270 ttc ccg gtg ggc gga cag ttc ctt gtt tcg gaa aac ccg gac gtg gtt       864
Phe Pro Val Gly Gly Gln Phe Leu Val Ser Glu Asn Pro Asp Val Val
                275                 280                 285 aat cac cat ctg gcg aag gtt tac ggt aaa gca tcc gtt ggc gca cca       912
Asn His His Leu Ala Lys Val Tyr Gly Lys Ala Ser Val Gly Ala Pro
            290                 295                 300 ccg atg tcg gtt ccg cat atc gat acc cgc gtt ctg gac ggt aaa cgc       960
Pro Met Ser Val Pro His Ile Asp Thr Arg Val Leu Asp Gly Lys Arg
            305                 310                 315 gta gtg ctg ttt ggg cca ttt gcc acc ttc tca acc aaa ttc ctc aaa      1008
Val Val Leu Phe Gly Pro Phe Ala Thr Phe Ser Thr Lys Phe Leu Lys
320                 325                 330 aac ggt tca ttg tgg gat cta atg agt tcc acc acc acc tct aac gtg      1056
Asn Gly Ser Leu Trp Asp Leu Met Ser Ser Thr Thr Thr Ser Asn Val
335                 340                 345                 350 atg ccg atg atg cac gtc ggg ctg gat aat ttc gat ctg gtg aaa tat      1104
Met Pro Met Met His Val Gly Leu Asp Asn Phe Asp Leu Val Lys Tyr
                355                 360                 365 ctg gtg agt cag gtg atg ttg agt gaa gag gat cgt ttt gaa gcg ttg      1152
Leu Val Ser Gln Val Met Leu Ser Glu Glu Asp Arg Phe Glu Ala Leu
            370                 375                 380 aaa gag tac tat ccg cag gcg aaa aaa gag gac tgg cgt ttg tgg caa      1200
Lys Glu Tyr Tyr Pro Gln Ala Lys Lys Glu Asp Trp Arg Leu Trp Gln
            385                 390                 395 gcg ggg cag cgc gtg cag att atc aag cgt gat gcc gag aaa ggt ggc      1248
Ala Gly Gln Arg Val Gln Ile Ile Lys Arg Asp Ala Glu Lys Gly Gly
400                 405                 410 gta ctg cgt ctg ggt act gaa gtc gtc agt gac cag caa gga acc att      1296
Val Leu Arg Leu Gly Thr Glu Val Val Ser Asp Gln Gln Gly Thr Ile
415                 420                 425                 430 gcc gcg ctc ctg ggg gca tcg cca ggg gcg tca acc gcc gcg ccg att      1344
Ala Ala Leu Leu Gly Ala Ser Pro Gly Ala Ser Thr Ala Ala Pro Ile
```

-continued

```
                435                 440                 445
atg ttg aat ctg ctg gaa aaa gta ttt ggc gat cgt gtt tcc agc ccg      1392
Met Leu Asn Leu Leu Glu Lys Val Phe Gly Asp Arg Val Ser Ser Pro
            450                 455                 460 caa tgg cag gct acg ttg aaa gcg atc gtt ccg tct tat gga cgc aag      1440
Gln Trp Gln Ala Thr Leu Lys Ala Ile Val Pro Ser Tyr Gly Arg Lys
        465                 470                 475 ctg aac ggt gat gta gcg gca aca gaa cgc gag ttg cag tac acc agc      1488
Leu Asn Gly Asp Val Ala Ala Thr Glu Arg Glu Leu Gln Tyr Thr Ser
    480                 485                 490 gaa gtg ctg ggg ttg aac tac gac aag ccg cag gca gca gat agt acg      1536
Glu Val Leu Gly Leu Asn Tyr Asp Lys Pro Gln Ala Ala Asp Ser Thr
495                 500                 505                 510 ccg aaa ccg cag ttg aaa ccg caa ccc gtt caa aaa gaa gtg gcg gat      1584
Pro Lys Pro Gln Leu Lys Pro Gln Pro Val Gln Lys Glu Val Ala Asp
                515                 520                 525 att gcg ttg taatgatacg ccacatccgg catggtatgc cggatgtggc             1633
Ile Ala Leu gtatgctgat aagacgcgcc agcgtcgcat caggcaaccg gctcgggcgt tagatgttgg    1693
atgcggcgta tcgggatcc tctagag                                          1720
```

<210> SEQ ID NO 2
<211> LENGTH: 529
<212> TYPE: PRT
<213> ORGANISM: Escherichia coli
<400> SEQUENCE: 2

```
Met Ala Ala Lys Ala Lys Ala Ser Glu Glu Gln Glu Thr Asp Val Leu
1               5                   10                  15

Leu Ile Gly Gly Gly Ile Met Ser Ala Thr Leu Gly Thr Tyr Leu Arg
            20                  25                  30

Glu Leu Glu Pro Glu Trp Ser Met Thr Met Val Glu Arg Leu Glu Gly
        35                  40                  45

Val Ala Gln Glu Ser Ser Asn Gly Trp Asn Asn Ala Gly Thr Gly His
    50                  55                  60

Ser Ala Leu Met Glu Leu Asn Tyr Thr Pro Gln Asn Ala Asp Gly Ser
65                  70                  75                  80

Ile Ser Ile Glu Lys Ala Val Ala Ile Asn Glu Ala Phe Gln Ile Ser
                85                  90                  95

Arg Gln Phe Trp Ala His Gln Val Glu Arg Gly Val Leu Arg Thr Pro
            100                 105                 110

Arg Ser Phe Ile Asn Thr Val Pro His Met Ser Phe Val Trp Gly Glu
        115                 120                 125

Asp Asn Val Asn Phe Leu Arg Ala Arg Tyr Ala Ala Leu Gln Gln Ser
    130                 135                 140

Ser Leu Phe Arg Gly Met Arg Tyr Ser Glu Asp His Ala Gln Ile Lys
145                 150                 155                 160

Glu Trp Ala Pro Leu Val Met Glu Gly Arg Asp Pro Gln Gln Lys Val
                165                 170                 175

Ala Ala Thr Arg Thr Glu Ile Gly Thr Asp Val Asn Tyr Gly Glu Ile
            180                 185                 190

Thr Arg Gln Leu Ile Ala Ser Leu Gln Lys Lys Ser Asn Phe Ser Leu
        195                 200                 205

Gln Leu Ser Ser Glu Val Arg Ala Leu Lys Arg Asn Asp Asp Asn Thr
    210                 215                 220
```

-continued

```
Trp Thr Val Thr Val Ala Asp Leu Lys Asn Gly Thr Ala Gln Asn Ile
225                 230                 235                 240

Arg Ala Lys Phe Val Phe Ile Gly Ala Gly Ala Ala Leu Lys Leu
                245                 250                 255

Leu Gln Glu Ser Gly Ile Pro Glu Ala Lys Asp Tyr Ala Gly Phe Pro
            260                 265                 270

Val Gly Gly Gln Phe Leu Val Ser Glu Asn Pro Asp Val Val Asn His
            275                 280                 285

His Leu Ala Lys Val Tyr Gly Lys Ala Ser Val Gly Ala Pro Pro Met
        290                 295                 300

Ser Val Pro His Ile Asp Thr Arg Val Leu Asp Gly Lys Arg Val Val
305                 310                 315                 320

Leu Phe Gly Pro Phe Ala Thr Phe Ser Thr Lys Phe Leu Lys Asn Gly
                325                 330                 335

Ser Leu Trp Asp Leu Met Ser Ser Thr Thr Thr Ser Asn Val Met Pro
                340                 345                 350

Met Met His Val Gly Leu Asp Asn Phe Asp Leu Val Lys Tyr Leu Val
                355                 360                 365

Ser Gln Val Met Leu Ser Glu Glu Asp Arg Phe Glu Ala Leu Lys Glu
            370                 375                 380

Tyr Tyr Pro Gln Ala Lys Lys Glu Asp Trp Arg Leu Trp Gln Ala Gly
385                 390                 395                 400

Gln Arg Val Gln Ile Ile Lys Arg Asp Ala Glu Lys Gly Gly Val Leu
                405                 410                 415

Arg Leu Gly Thr Glu Val Val Ser Asp Gln Gln Gly Thr Ile Ala Ala
                420                 425                 430

Leu Leu Gly Ala Ser Pro Gly Ala Ser Thr Ala Ala Pro Ile Met Leu
            435                 440                 445

Asn Leu Leu Glu Lys Val Phe Gly Asp Arg Val Ser Ser Pro Gln Trp
            450                 455                 460

Gln Ala Thr Leu Lys Ala Ile Val Pro Ser Tyr Gly Arg Lys Leu Asn
465                 470                 475                 480

Gly Asp Val Ala Ala Thr Glu Arg Glu Leu Gln Tyr Thr Ser Glu Val
                485                 490                 495

Leu Gly Leu Asn Tyr Asp Lys Pro Gln Ala Ala Asp Ser Thr Pro Lys
            500                 505                 510

Pro Gln Leu Lys Pro Gln Pro Val Gln Lys Glu Val Ala Asp Ile Ala
            515                 520                 525

Leu
```

<210> SEQ ID NO 3
<211> LENGTH: 25
<212> TYPE: DNA
<213> ORGANISM: Artificial sequence
<220> FEATURE:
<223> OTHER INFORMATION: Description of the artificial sequence: Primer
      YojH1

<400> SEQUENCE: 3
gcggaattcg atggcggcaa aagcg                                      25

<210> SEQ ID NO 4
<211> LENGTH: 20
<212> TYPE: DNA
<213> ORGANISM: Artificial sequence
<220> FEATURE:
<223> OTHER INFORMATION: Description of the artificial sequence: Primer

```
         YojH2

<400> SEQUENCE: 4
gttacgccgc atccaacatc                                              20

<210> SEQ ID NO 5
<211> LENGTH: 20
<212> TYPE: DNA
<213> ORGANISM: Artificial sequence
<220> FEATURE:
<223> OTHER INFORMATION: Description of the artificial sequence: Primer
      Tdh1

<400> SEQUENCE: 5
tcgcgaccta taagtttggg                                              20

<210> SEQ ID NO 6
<211> LENGTH: 20
<212> TYPE: DNA
<213> ORGANISM: Artificial sequence
<220> FEATURE:
<223> OTHER INFORMATION: Description of the artificial sequence: Primer
      Tdh2

<400> SEQUENCE: 6
aataccagcc cttgttcgtg                                              20

<210> SEQ ID NO 7
<211> LENGTH: 24
<212> TYPE: DNA
<213> ORGANISM: Artificial sequence
<220> FEATURE:
<223> OTHER INFORMATION: Description of the artificial sequence: Primer
      YOJH1a

<400> SEQUENCE: 7
ggatccgttg atgccgcgca aatc                                         24

<210> SEQ ID NO 8
<211> LENGTH: 48
<212> TYPE: DNA
<213> ORGANISM: Artificial sequence
<220> FEATURE:
<223> OTHER INFORMATION: Description of the artificial sequence: Primer
      YCHIS

<400> SEQUENCE: 8
cgcgaattct tagtggtggt ggtggtggtg caacgcaata tccgccac               48

<210> SEQ ID NO 9
<211> LENGTH: 20
<212> TYPE: DNA
<213> ORGANISM: Artificial sequence
<220> FEATURE:
<223> OTHER INFORMATION: Description of the artificial sequence: Primer
      Y_01

<400> SEQUENCE: 9
gctggatgaa tgggcggcgg                                              20

<210> SEQ ID NO 10
<211> LENGTH: 27
<212> TYPE: DNA
<213> ORGANISM: Artificial sequence
<220> FEATURE:
<223> OTHER INFORMATION: Description of the artificial sequence: Primer
      Y_04
```

-continued

```
<400> SEQUENCE: 10
cgcggatccc cggtttcaac gatgatg                                          27

<210> SEQ ID NO 11
<211> LENGTH: 6
<212> TYPE: PRT
<213> ORGANISM: Corynebacterium glutamicum
<220> FEATURE:
<223> OTHER INFORMATION: N-Terminus of the malate:quinone oxidoreductase
      protein B.

<400> SEQUENCE: 11

Leu Asn Ala Val Ser Met
  1               5

<210> SEQ ID NO 12
<211> LENGTH: 7
<212> TYPE: PRT
<213> ORGANISM: Corynebacterium glutamicum
<220> FEATURE:
<223> OTHER INFORMATION: N-Terminus of the malate:quinone oxidoreductase
      protein C.

<400> SEQUENCE: 12

Ala Val Ser Met Ala Ala Lys
  1               5
```

PROCESS FOR THE FERMENTATIVE PREPARATION OF L-THREONINE

This application claims the benefit of Provisional Application No. 60/229,329, filed Sep. 1, 2000.

This invention relates to the new amino acid sequence of the malate:quinone oxidoreductase enzyme protein (Mqo) of Enterobacteriaceae and to a process for the fermentative preparation of L-threonine using Enterobacteriaceae in which the mqo gene is enhanced.

PRIOR ART

L-Threonine is used in animal nutrition, in human medicine and in the pharmaceuticals industry. It is known that L-threonine can be prepared by fermentation of strains of Enterobacteriaceae, in particular *Escherichia coli* and *Serratia marcescens*. Because of their great importance, work is constantly being undertaken to improve the preparation processes. Improvements to the process can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the threonine analogue α-amino-β-hydroxyvaleric acid (AHV), or are auxotrophic for metabolites of regulatory importance and produce L-threonine are obtained in this manner.

Methods of the recombinant DNA technique have also been employed for some years for improving the strain of Enterobacteriaceae strains which produce L-threonine, by amplifying individual threonine biosynthesis genes and investigating the effect on the L-threonine production.

OBJECT OF THE INVENTION

The inventors had the object of providing new measures for improved fermentative preparation of L-threonine.

DESCRIPTION OF THE INVENTION

The invention provides a polypeptide from Enterobacteriaceae with malate:quinone oxidoreductase (Mqo) activity (E.C. 1.1.99.16) chosen from the group consisting of a) polypeptide with the amino acid sequence shown in SEQ ID NO. 2, or b) polypeptide which is at least 70%, preferably at least 80%, particularly preferably at least 90 to 95% identical to the amino acid sequence shown in SEQ ID NO. 2, or c) polypeptide according to SEQ ID NO. 2, including deletion, insertion or exchange of one or more amino acids, or d) polypeptide according to SEQ ID NO. 2, including N- or C-terminal lengthening by one or more amino acids, the total length of the polypeptide according to b), c) or d) being at least 514 and at most 544, preferably at least 519 and at most 539, in a preferred form at least 524 and at most 534, particularly preferably at least 527 and at most 531 amino acid radicals.

The invention furthermore provides a polynucleotide from Enterobacteriaceae which codes for a polypeptide with malate:quinone oxidoreductase (Mqo) activity (E.C. 1.1.99.16), chosen from the group consisting of a) DNA which contains the nucleotide sequence corresponding to nucleobases 7 to 1593 of SEQ ID NO. 1, or b) DNA according to a) corresponding to the degeneration of the genetic code, or c) DNA according to a) containing sense mutations of neutral function, or d) DNA which is at least 70%, preferably at least 80%, particularly preferably at least 90 to 95% identical to that mentioned in a) or b), or e) polynucleotide which hybridizes with the DNA according to a), b), c) or d).

Figure 1:
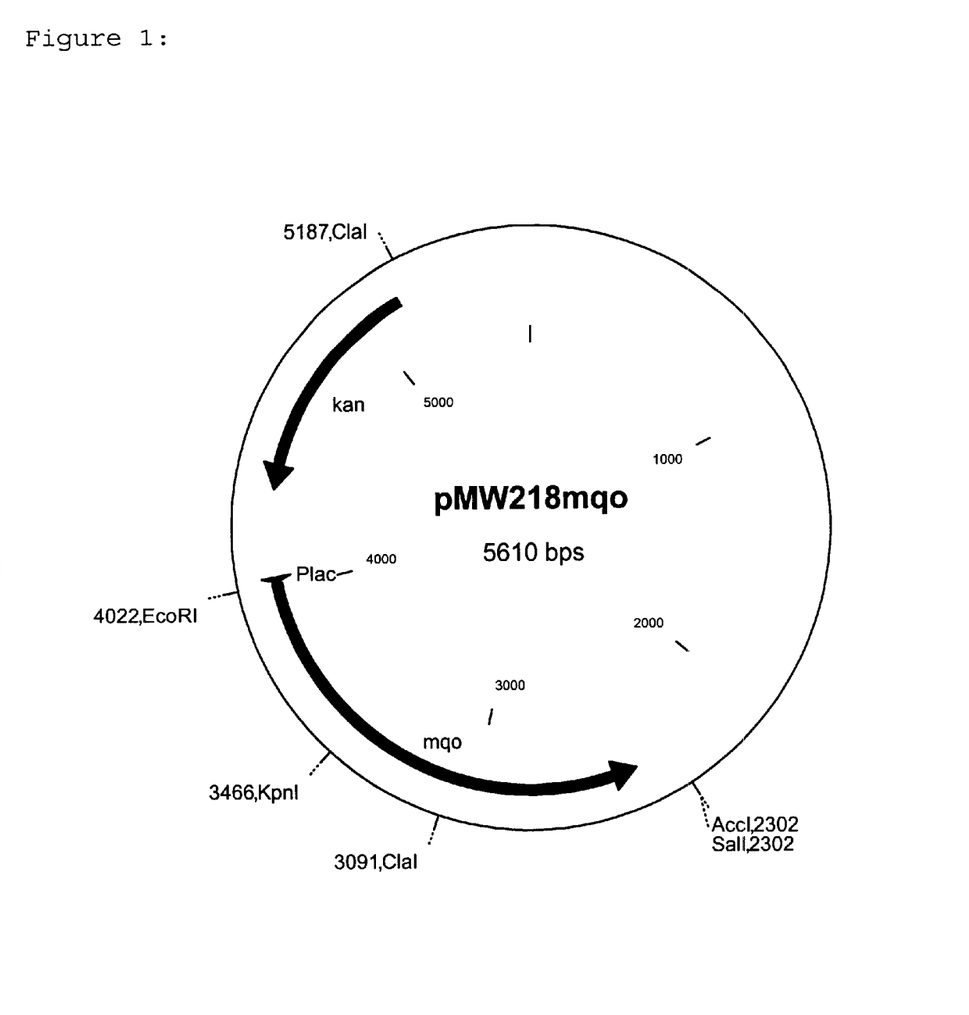
FIG. 1: Map of the plasmid pMW218mqo containing the mqo gene.

The invention also provides a DNA which is capable of replication and codes for the polypeptide shown in SEQ ID NO. 2, a vector containing the mqo gene corresponding to nucleobases 7 to 1593 of SEQ ID NO. 1, in particular plasmid pMW218mqo shown in FIG. 1.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include the polypeptides according to SEQ ID NO. 2, which have malate:quinone oxidoreductase activity, and also those which are at least 70%, preferably at least 80% and in particular at least 90% to 95% identical to the polypeptide according to SEQ ID NO. 2 and have the activity mentioned.

Finally, the invention provides a process for the fermentative preparation of L-threonine using Enterobacteriaceae which in particular already produce L-threonine and in which the nucleotide sequence(s) which code(s) for the mqo gene are enhanced, in particular over-expressed.

In particular, the process is a process for the preparation of L-threonine, which comprises carrying out the following steps:

a) fermentation of microorganisms of the family Enterobacteriaceae in which at least the mqo gene is enhanced (over-expressed), optionally in combination with further genes, b) concentration of the L-threonine in the medium or in the cells of the microorganisms of the family Enterobacteriaceae, and c) isolation of the L-threonine.

The term "enhancement" in this connection describes the increase in the intracellular activity of one or more enzymes or proteins in a microorganism which are coded by the corresponding DNA, for example by increasing the number of copies of the gene or genes, using a potent promoter or a gene which codes for a corresponding enzyme or protein with a high activity, and optionally combining these measures.

The microorganisms which the present invention provides can prepare L-threonine from glucose, sucrose, lactose, fructose, maltose, molasses, starch, or from glycerol and ethanol. They are representatives of Enterobacteriaceae, in particular of the genera Escherichia and Serratia. Of the genus Escherichia the species *E. coli* and of the genus Serratia the species *Serratia marcescens* are to be mentioned in particular.

Suitable L-threonine-producing strains of the genus Escherichia, in particular of the species *E. coli*, are, for example

*Escherichia coli* TF427
*Escherichia coli* H4578
*Escherichia coli* KY10935
*Escherichia coli* EL1003
*Escherichia coli* VNIIgenetika MG-442
*Escherichia coli* VNIIgenetika VL334/pYN7
*Escherichia coli* VNIIgenetika M1
*Escherichia coli* VNIIgenetika 472T23
*Escherichia coli* VNIIgenetika TDH-6
*Escherichia coli* BKIIM B-3996
*Escherichia coli* BKIIM B-5318
*Escherichia coli* B-3996-C43
*Escherichia coli* B-3996-C80
*Escherichia coli* B-3996/pTWV-pps
*Escherichia coli* B-3996(pMW::THY)
*Escherichia coli* B-3996/pBP5
*Escherichia coli* kat 13
*Escherichia coli* KCCM-10132

Suitable L-threonine-producing strains of the genus Serratia, in particular of the species *Serratia marcescens*, are, for example

*Serratia marcescens* HNr21
*Serratia marcescens* TLr156
*Serratia marcescens* T2000

The nucleotide sequence of the chromosome of *E. coli* is known and is available in databanks accessible to the public, such as, for example, the databank of the European Molecular Biology Laboratories (EMBL, Heidelberg, Germany). Examples of such sequences deposited are the entries accessible under number AE000310 or D90850.

In the work on the present invention it was possible to identify the mqo gene, which codes for malate:quinone oxidoreductase, of *E. coli* (SEQ ID NO. 1) and the amino acid sequence of the Mqo enzyme protein formed (SEQ ID NO. 2).

It has furthermore been possible to isolate two further new malate:quinone oxidoreductase [sic] proteins, designated protein B and C, which have the N-terminal amino acid sequence shown in SEQ ID No. 11 and 12. These are also provided by the invention.

It has been found that Enterobacteriaceae produce L-threonine in an improved manner after over-expression of the mqo gene, which codes for malate:quinone oxidoreductase (E.C. 1.1.99.16).

According to the invention, it is also possible to use a DNA section which contains the DNA sequence of the gene of the malate:quinone oxidoreductase given in the databank of the National Center for Biotechnology Information (NCBI, Bethesda, Md., USA) with accession number P33940.

Alleles of the mqo gene which result from the degeneracy of the genetic code or due to "sense mutations" of neutral function can furthermore be used. It is also known that the amino acid methionine or formylmethionine coded by the start codon ATG can be removed in various proteins by enzymes of the host.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-threonine production. The expression is likewise improved by measures to prolong the life of the m-RNA. Furthermore, the enzyme activity is also increased by preventing the degradation of the enzyme protein. The genes or gene constructions can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Chang and Cohen (Journal of Bacteriology 134:1141–1156 (1978)), in Hartley and Gregori (Gene 13:347–353 (1981)), in Amann and Brosius (Gene 40:183–190 (1985)), in de Broer et al. (Proceedings of the National (sic) of Sciences of the United States of America 80:21–25 (1983)), in LaVallie et al. (BIO/TECHNOLOGY 11, 187–193 (1993)), in WO 98/04715, in Llosa et al. (Plasmid 26:222–224 (1991)), in Quandt and Klipp (Gene 80:161–169 (1989)), in Hamilton (Journal of Bacteriology 171:4617–4622 (1989), in Jensen and Hammer (Biotechnology and Bioengineering 58, 191–195 (1998) and in known textbooks of genetics and molecular biology.

Plasmid vectors which are capable of replication in Enterobacteriaceae, such as e.g. cloning vectors derived from pACYC184 (Bartolomé et al.; Gene 102, 75–78 (1991)), pTrc99A, which is described by Amann et al. (Gene 69:301–315 (1988)), or pSC101 derivatives (Vocke and Bastia, Proceedings of the National Academy of Science, USA 80 (21):6557–6561 (1983)) can be used. A strain transformed with a plasmid vector where the plasmid vector carries the nucleotide sequence which codes for the mqo gene can be employed in a process according to the invention.

In addition, it may be advantageous for the production of L-threonine with strains of the family Enterobacteriaceae to enhance, in particular to over-express, one or more enzymes of the known threonine biosynthesis pathway or enzymes of anaplerotic metabolism or enzymes for the production of reduced nicotinamide adenine dinucleotide phosphate, in addition to the mqo gene.

Thus, for example, one or more genes chosen from the group consisting of the thrABC operon which codes for aspartate kinase, homoserine dehydrogenase, homoserine kinase and threonine synthase (U.S. Pat. No. 4,278,765), the pyc gene which codes for pyruvate carboxylase (DE-A-19 831 609), the pps gene which codes for phosphoenol pyruvate synthase (Molecular and General Genetics 231:332 (1992)), the ppc gene which codes for phosphoenol pyruvate carboxylase (Gene 31:279–283 (1984)), the genes pntA and pntB which code for transhydrogenase (European Journal of Biochemistry 158:647–653 (1986)), the rhtB gene which imparts homoserine resistance (EP-A-0994190)

the rhtC gene which imparts threonine resistance (EP-A-1013765), and the gdhA gene which codes for glutamate dehydrogenase (Gene 27:193–199 (1984))

can be enhanced, in particular over-expressed, at the same time.

It may furthermore be advantageous for the production of L-threonine, in addition to the enhancement of the mqo gene, for one or more of the genes chosen from the group consisting of:

the tdh gene which codes for threonine dehydrogenase (Ravnikar and Somerville, Journal of Bacteriology 169, 4716–4721 (1987)), the mdh gene which codes for malate dehydrogenase (E.C. 1.1.1.37)

to be attenuated, in particular to be eliminated or for the expression thereof to be reduced at the same time.

Finally, in addition to enhancement of the mqo gene it may be advantageous for the production of L-threonine to eliminate undesirable side reactions, (Nakayama: "Breeding of Amino Acid Producing Microorganisms", in: Overproduction of Microbial Products, Krumphanzl, Sikyta, Vanek (eds.), Academic Press, London, UK, 1982). Bacteria in which the metabolic pathways which reduce the formation of L-threonine are at least partly eliminated can be employed in a process according to the invention.

The microorganisms produced according to the invention can be cultured in the batch process (batch culture) or in the fed batch [sic] (feed process). A summary of known culture methods are [sic] described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and optionally cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. Culturing is continued until a maximum of L-threonine has formed. This target is usually reached within 10 hours to 160 hours.

The analysis of L-threonine can be carried out by anion exchange chromatography with subsequent ninhydrin derivatization, as described by Spackman et al. (Analytical Chemistry, 30, (1958), 1190), or it can take place by reversed phase HPLC as described by Lindroth et al. (Analytical Chemistry (1979) 51: 1167–1174).

A pure culture of the L-threonine-producing strain B-3996kurΔtdh/pVIC40, pMW218mqo was deposited on Jan. 24, 2001 at the Deutsche Sammlung für Mikrorgansimen [sic] und Zellkulturen (DSMZ=German Collection of Microorganisms and Cell Cultures, Braunschweig, Germany) as DSM 14004.

The process according to the invention is used for the fermentative preparation of amino acids, in particular L-threonine and L-isoleucine.

The present invention is explained in more detail in the following with the aid of embodiment examples.

The isolation of plasmid DNA from *E. coli* and all techniques of restriction, Klenow and alkaline phosphatase treatment are carried out by the method of Sambrook et al. (Molecular cloning—A laboratory manual (1989) Cold Spring Harbour Laboratory Press). Unless described otherwise, the transformation of *E. coli* is carried out by the method of Chung et al. (Proceedings of the National Academy of Sciences of the United States of America USA (1989) 86:2172–2175).

The incubation temperature during preparation of strains and transformants is 37° C. Temperatures of 30° C. and 44° C. are used in the gene replacement process according to Hamilton et. al.

EXAMPLE 1

Construction of the Expression Plasmid pMW218mqo

The mqo gene from *E. coli* K12 is amplified using the polymerase chain reaction (PCR) and synthetic oligonucleotides. Starting from the nucleotide sequence of the yojH gene in *E. coli* K12 MG1655 (EMBL AE000310), PCR primers (see SEQ ID No. 3 and 4) are synthesized (MWG Biotech, Ebersberg, Germany):

```
YojH1:    5'-GCGGAATTCGATGGCGGCAAAAGCG-3'

YojH2:    5'-GTTACGCCGCATCCAACATC-3'
```

The chromosomal *E. coli* K12 MG1655 DNA employed for the PCR is isolated according to the manufacturers instructions with "QIAGEN Genomic-tips 100/G" (QIAGEN, Hilden, Germany). A DNA fragment approx. 1700 base pairs (bp) in size can be amplified with the specific primers under standard PCR conditions (Innis et al. (1990) PCR protocols. A guide to methods and applications, Academic Press) with Pfu-DNA polymerase (Promega Corporation, Madison, USA). The PCR product is cleaved with the enzyme EcoRI and ligated with the plasmid pMW218 (Nippon Gene, Toyama, Japan), which is cleaved with the enzymes EcoRI and SmaI. The *E. coli* strain DH5α is transformed with the ligation batch and plasmid-carrying cells are selected on LB agar (Lennox, Virology 1:190 (1955)), to which 20 μg/ml kanamycin is added. Successful cloning of the mqo gene can be demonstrated after plasmid DNA isolation and control cleavage with EcoRI, AccI and ClaI. The plasmid is designated pMW218mqo (FIG. 1).

EXAMPLE 2
Preparation of L-threonine with the Strain MG442/pMW218mqo 2.1 Preparation of the Strain MG442/pMW218mqo The L-threonine-producing *E. coli* strain MG442 is described in U.S. Pat. No. 4,278,765 and deposited as CMIM B-1628 at the Russian National Collection for Industrial Microorganisms (VKPM, Moscow, Russia).

The strain MG442 is transformed with the plasmid pMW218mqo and plasmid-carrying cells are selected on LB agar supplemented with 20 µg/ml kanamycin. The strain is designated MG442/pMW218mqo.

2.2 Preparation of L-threonine

Selected individual colonies of MG442/pMW218mqo are multiplied further on minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 25 mg/l isoleucine, 2 g/l glucose, 20 g/l agar, 20 mg/l kanamycin. The formation of L-threonine is checked in batch cultures of 10 ml contained in 100 ml conical flasks. For this, 10 ml of preculture medium of the following composition: 2 g/l yeast extract, 10 g/l $(NH_4)_2SO_4$, 0.5 g/l $MgSO_4*7H_2O$, 15 g/l $CaCO_3$, 20 g/l glucose, 20 mg/l kanamycin are inoculated and the batch is incubated for 16 hours at 37° C. and 180 rpm on an ESR incubator from Kühner AG (Birsfelden, Switzerland). In each case 250 µl of this preculture are transinoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 25 mg/l isoleucine, 30 g/l $CaCO_3$, 20 g/l glucose) and the batch is incubated for 48 hours at 37° C. After the incubation the optical density (OD) of the culture suspension is determined with an LP2W photometer from the company Dr. Lange (Berlin, Germany) at a measurement wavelength of 660 nm.

The concentration of L-threonine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in table 1.

TABLE 1

| Strain | OD (660 nm) | L-Threonine g/l |
|---|---|---|
| MG442 | 4.7 | 0.46 |
| MG442/pMW218mqo | 4.5 | 0.89 |

EXAMPLE 3
Preparation of L-threonine with the strain B-3996kurαtdh/pVIC40, pMW218mqo The L-threonine-producing *E. coli* strain B-3996 is described in U.S. Pat. No. 5,175,107 and deposited at the Russian National Collection for Industrial Microorganisms (VKPM, Moscow, Russia).

3.1 Preparation of the Strain B-3996kurΔtdh/pVIC40, pMW218mqo

After culture in antibiotic-free complete medium for approximately ten generations, a derivative of strain B-3996 which no longer contains the plasmid pVIC40 is isolated. The strain formed is streptomycin-sensitive and is designated B-3996kur.

The method described by Hamilton et al. (Journal of Bacteriology (1989) 171: 4617–4622), which is based on the use of the plasmid pMAK705 with a temperature-sensitive replicon, is used for incorporation of a deletion into the tdh gene. The plasmid pDR121 (Ravnikar and Somerville, Journal of Bacteriology (1987) 169:4716–4721) contains a DNA fragment from *E. coli* 3.7 kilo-base pairs (kbp) in size, on which the tdh gene is coded. To generate a deletion of the tdh gene region, pDR121 is cleaved with the restriction enzymes ClaI and EcoRV and the DNA fragment 5 kbp in size isolated is ligated, after treatment with Klenow enzyme. The ligation batch is transformed in the *E. coli* strain DH5α and plasmid-carrying cells are selected on LB agar, to which 50 µg/ml ampicillin are added.

Successful deletion of the tdh gene can be demonstrated after plasmid DNA isolation and control cleavage with EcoRI. The EcoRI fragment 1.7 kbp in size is isolated, and ligated with the plasmid pMAK705, which is partly digested with EcoRI. The ligation batch is transformed in DH5α and plasmid-carrying cells are selected on LB agar, to which 20 µg/ml chloramphenicol are added. Successful cloning is demonstrated after isolation of the plasmid DNA and cleavage with EcoRI. The pMAK705 derivative formed is designated pDM32.

For the gene replacement, B-3996kur is transformed with the plasmid pDM32. The replacement of the chromosomal tdh gene with the plasmid-coded deletion construct is carried out by the selection process described by Hamilton et al. and is verified by standard PCR methods (Innis et al. (1990), PCR Protocols. A Guide to Methods and Applications, Academic Press) with the following oligonucleotide primers (see SEQ ID No. 5 and 6).

```
Tdh1:     5'-TCGCGACCTATAAGTTTGGG-3'

Tdh2:     5'-AATACCAGCCCTTGTTCGTG-3'.
```

The strain formed is tested for kanamycin sensitivity and is designated B-3996kurΔtdh.

B-3996kurΔtdh is transformed with the plasmid pVIC40 isolated from B-3996 and plasmid-carrying cells are selected on LB agar with 20 µg/ml streptomycin. A selected individual colony is designated B-3996kurΔtdh/pVIC40 and transformed with the plasmid pMW218mqo. Selection is carried out on LB-agar to which 20 µg/ml streptomycin and 50 µg/ml kanamycin are added. The strain formed in this way is designated B-3996kurΔtdh/pVIC40, pMW218mqo.

3.2 Preparation of L-threonine

The preparation of L-threonine by the strains B-3996kurΔtdh/pVIC40 and B-3996kurΔtdh/pVIC40, pMW218mqo is tested as described in example 2, the minimal medium and the production medium not being supplemented with L-isoleucine. The minimal medium, the preculture medium and the production medium are supplemented with 20 µg/ml streptomycin for B-3996kurΔtdh/pVIC40 and with 20 µg/ml streptomycin and 50 µg/ml kanamycin for B-3996kurΔtdh/pVIC40, pMW218mqo.

The result of the experiment is summarized in table 2.

TABLE 2

| Strain | OD (660 nm) | L-Threonine |
|---|---|---|
| B-3996kurΔtdh/pVIC40 | 4.7 | 6.26 |
| B-3996kurΔtdh/pVIC40, pMW218mqo | 3.7 | 7.72 |

EXAMPLE 4
Preparation of a vector containing a histidine-tagged malate:quinone oxidoreductase gene of *E. coli*

1744 bp DNA fragment, which codes for the malate:quinone oxidoreductase protein extended by a six-fold histidine radical on the C-terminal end, was prepared by means of the polymerase chain reaction (PCR) and then cloned.

The primer YOJH1a (SEQ ID No 7) was drafted with the aid of the known nucleotide sequence with Accession Number AE000310 (EMBL, European Molecular Biology Laboratories, Heidelberg, Germany). This primer has the sequence:

5'-GGA TCC GTT GAT GCC GCG CAA ATC-3'.

The primer YCHIS (SEQ ID No 8), which has the following sequence, was employed as the second primer:

5'-CGC GAA TTC TTA GTG GTG GTG GTG GTG GTG CAA CGC AAT ATC CGC CAC-3'.

The primers shown were synthesized by MWG Biotech (Ebersberg, Germany). The PCR reaction was carried out by the standard PCR method of Innis et al., (PCR Protocols. A Guide to Methods and Applications, 1990, Academic Press, New York, USA).

Whole DNA isolated from a colony of the E. coli strain MC4100 (Casadaban et al. Journal of Molecular Biology 104, 541–555, 1976) served as the template.

The PCR was carried out in a Thermocycler from Techne (Cambridge, UK). The samples were first denatured for 5 minutes at 94° C. and the Taq polymerase from Promega (Madison, Wis., USA) was then added to the sample batch. A cycle comprising denaturing (60 seconds, 94° C.), annealing (60 seconds, 60° C.) and synthesis (120 seconds, 72° C.) was then passed through 10 times, the annealing temperature being increased by 0.4° C. in each cycle. The subsequent 25 cycles comprised denaturing (60 seconds, 94° C.), annealing (60 seconds, 64° C.) and synthesis (120 seconds, 72° C.). Finally, a concluding synthesis of 10 minutes at 72° C. was carried out.

The DNA fragment 1744 bp in length containing the mqo gene amplified in this manner was purified with the aid of the QIAQuick PCR Purification Kit from Qiagen (Hilden, Germany) and then digested with the restriction enzymes BamHI and EcoRI. These restriction cleavage sites were generated during the PCR with the aid of the primers YOJHI and YCHIS. After gel electrophoresis, the digested DNA fragment was cut out of the agarose gel and purified with QIAEX II Gel Extraction Kit (155) (Hilden, Germany), mixed into the vector pUC19 treated with the restriction enzymes BamHI and EcoRI (Yanisch-Perron et al., Gene 33, 103–119, 1985) and then treated with T4 DNA ligase.

An E. coli strain designated MC4100Δmqo, which contains a deletion in the mqo gene and was prepared according to the prior art, was used as the cloning host for the transformation. For this, the mqo gene was first amplified with the aid of the primers Y_01 (SEQ ID No 9) and Y_04 (SEQ ID No 10) using whole DNA isolated from strain MC4100, with the aid of the PCR method The PCR conditions comprised 30 cycles of denaturing (30 seconds, 94° C.), annealing (30 seconds, 60° C.) and synthesis (2 minutes, 72° C.)

The primer Y_01 has the following sequence:
5'-GCTGGATGAATGGGCGGCGG-3'

The primer Y_04 has the following sequence:
5'-CGCGGATCCCCGGTTTCAACGATGATG-3'

The amplified DNA fragment contains a cleavage site for the restriction enzyme BamHI directly after the primer Y_01. The BamHI restriction cleavage site contained in the oligonucleotide primer Y_04 is identified by underlining. The amplified DNA fragment was digested with BamHI and then incorporated into the BamHI cleavage site of the plasmid pKO3 described by Link et al. (Journal of Bacteriology 179, 6228–6237 (1997)). The resulting plasmid was designated pKO3mqo and treated with the restriction enzyme MluI in order to remove an internal DNA segment of the mqo gene 416 bp long (deletion). The plasmid pKO3Δmqo obtained in this manner was used for incorporation of the deletion Δmqo in the strain MC4100. The method described by Link et al (Journal of Bacteriology 179, 6228–6237 (1997)) was employed for this.

The strain MC4100Δmqo was transformed with the ligation mixture described above. Transformants were selected on LB medium, which had been supplemented with 100 μg/ml carbenicillin. A plasmid was isolated from a transformant and designated pUCH2. Plasmid pUCH2 contains a DNA fragment 1744 bp long, which codes for the malate-:quinone oxidoreductase protein extended by a six-fold histidine radical on the C-terminal end.

EXAMPLE 5

Isolation and purification of the over-expressed histidine-tagged malate:quinone oxidoreductase Five times, 200 ml LB medium were treated with 100 μg/ml carbenicillin and 100 μM isopropyl β-D-thiogalactoside (IPTG), inoculated with in each case a colony of the strain MC4100Δmqo/pUCH2 and in each case cultured in 1 l conical flasks for 16 hours at 37° C. and 200 revolutions per minute. The cells were washed twice in buffer A (50 mM hepes, 10 mM potassium acetate, 10 mM $CaCl_2$, 5 mM $MgCl_2$, adjusted to pH 7.5 with NaOH) at 4° C. and resuspended in 40 ml of the same buffer. The cells were then broken down twice in a precooled French Pressure Cell from Spectronic Unicam (Rochester, N.Y., USA) under 69 MPa (mega-Pascal). The cell debris was then sedimented twice in a centrifuge at 4° C. for 10 minutes at 10000×g. The supernatant was then centrifuged for 30 minutes at 75000×g and 4° C. The membrane pellet was resuspended with the same volume of buffer B (50 mM Na phosphate, 200 mM NaCl, pH 7.5) and centrifuged again for 30 minutes at 75000×g and 4° C. The pellet was then resuspended with 1 ml buffer B. The histidine-tagged malate:quinone oxidoreductase protein was purified in two steps.

Step 1: Solubilization:

2% Triton X-100 and 10% glycerol were added to the resuspended membranes and the batch was incubated for 10 minutes on ice. The batch was then centrifuged for 30 minutes at 200000×g at 4° C.

Step 2: Affinity Chromatography:

The equilibration of the "Talon-Metal-Affinity Resin" column material (500 μl column volume, CLONTECH Laboratories, Palo Alto, USA) was carried out twice with 1 ml buffer B and once with 1 ml buffer C (50 mM Na phosphate, 200 mM NaCl, 0.05% Triton X-100, 10 μM flavin adenine dinucleotide (FAD), 0.2 mg/ml phospholipid, pH 7.0). The phospholipid used was L-αphosphatidylethanolamine, type IX from E. coli (Sigma-Aldrich, Deisenhofen, Germany), which was mixed as a 30 mg/ml stock solution in deionized water and treated briefly with an ultrasound apparatus (BRANSON Sonifier Cell Disrupter B15) for a few seconds until the suspension was transparent. The supernatant (1 ml) from step 1 was applied to the equilibrated column and incubated for 20 minutes at room temperature. Thereafter, the column was flushed five times with buffer D (50 mM Na phosphate, 200 mM NaCl, 0.05% Triton X-100, 10% glycerol, 10 μM FAD, 0.2 mg/ml phospholipid, 10 mM imidazole, pH 7.0) and then eluted twice with 500 μl buffer E (50 mM Na phosphate, 200 mM NaCl, 0.05% Triton X-100, 10% glycerol, 10 μM FAD, 0.2 mg/ml phospholipid, 100 mM imidazole, pH 7.0). The two fractions were combined and a buffer exchange was carried out by means of an ULTRAFREE-0.5 Centrifugal Filter Device (Millipore Corporation, Bedford, Mass., USA), in order to remove the imidazole and to reduce the volume to 500 μl. A second affinity chromatography was then carried out with the "Talon-Metal-Affinity Resin" column material (250 μl column volume), as described above. The purified protein was stored at −20° C.

The purified malate:quinone oxidoreductase protein was investigated by means of SDS polyacrylamide gel electrophoresis and subsequent staining with Coomassie blue. In this analysis, two protein bands (protein B and protein C) with the mobility corresponding to a molecular weight of about 60±2 KD (kilo-Dalton) were detected. The two proteins were blotted on to a polyvinylidene difluoride (PVDF) membrane (Boehringer Mannheim, Mannheim, Germany) and stained with Coomassie blue. The two protein bands were then cut out of the blot membrane.

EXAMPLE 6

Determination of the N-position Amino Acid Sequence

The N-position amino acid sequences of the malate:quinone oxidoreductase protein B and protein C were determined by Edman degradation (Edman, Molecular Biology Biochemistry Biophysics 8:211–55(1970)) by means of the automatic sequencer Procise Sequencer from PE Biosystems (Foster City, Calif., USA). For protein B the amino acid sequence L N A V S M (see also SEQ ID No. 11) and for protein C the amino acid sequence A V S M A A K (see also SEQ ID No. 12) was determined.

The following figures are attached.

The length data are to be understood as approx. data. The abbreviations and designations used have the following meaning.

Plac: Promoter sequence of the lactose operon

Kan: Kanamycin resistance gene

The abbreviations for the restriction enzymes have the following meaning

AccI: Restriction endonuclease from *Acinetobacter calcoaceticus*

ClaI: Restriction endonuclease from *Caryphanon latum*

EcoRI: Restriction endonuclease from *E. coli*

KpnI: Restriction endonuclease from *Klebsiella pneumoniae*

SalI: Restriction endonuclease from *Streptomyces albus*

What is claimed is:

1. A vector comprising an isolated polynucleotide native to the species *Escherichia coli,* wherein said polynucleotide encodes a polypeptide comprising the amino acid sequence of SEQ ID NO:2, and wherein said polypeptide has malate:quinone oxidoreductase activity.

2. The vector of claim 1, wherein said polypeptide consists of the amino acid sequence of SEQ ID NO:2 and has malate:quinone oxidoreductase activity.

3. The vector of claim 1, wherein said polynucleotide comprises SEQ ID NO:1.

4. The vector of claim 1, wherein said polynucleotide consists of SEQ ID NO:1.

5. The plasmid pMW12mqo which contains the mqo gene of *E. coli* as set forth in SEQ ID NO:1.

6. The vector of any one of claims 1 to 5, wherein said polypeptide comprises the amino acid sequence of SEQ ID NO:2 and a N-terminal extension comprising the amino acid sequence of SEQ ID NO: 11 or SEQ ID NO: 12, and wherein the number of amino acids of said polypeptide does not exceed 544.

7. A transformed L-threonine producing strain of genus Escherichia comprising the vector of any one of claims 1 to 5.

8. A transformed L-threonine producing strain of genus Escherichia comprising the any one of claim 6.

9. A transformed L-threonine producing strain of genus Escherichia, comprising the isolated polynucleotide of SEQ ID NO:1 which encodes a polypeptide comprising the amino acid sequence of SEQ ID NO:2, wherein said polypeptide has malate:quinone oxidoreductase activity.

10. The transformed bacterium of claim 9, wherein said polypeptide comprises the amino acid sequence of SEQ ID NO:2 and a N-terminal extension comprising the amino acid sequence of SEQ ID NO: 11 or SEQ ID NO: 12, and wherein the number of amino acids of said polypeptide does not exceed 544.

11. The transformed bacterium of claim 9, wherein said polynucleotide is in several copies.

12. The transformed bacterium of claim 9, wherein said polynucleotide is overexpressed.

13. A biologically pure culture of *Escherichia coli* strain B-3996kurΔtdh/pVIC40, pMW218mqo deposited as DSM 14004.

* * * * *